United States Patent [19]

Dean et al.

[11] Patent Number: 5,405,597
[45] Date of Patent: Apr. 11, 1995

[54] TECHNETIUM-99M LABELED SOMATOSTATIN-DERIVED PEPTIDES FOR IMAGING

[75] Inventors: Richard T. Dean; John Lister-James, both of Bedford; Scott Buttram, Derry, all of N.H.

[73] Assignee: Diatech, Inc., Londonderry, N.H.

[21] Appl. No.: 977,628

[22] Filed: Nov. 17, 1992

Related U.S. Application Data

[62] Division of Ser. No. 757,470, Sep. 10, 1991, Pat. No. 5,225,180.

[51] Int. Cl.⁶ ............................................. A61K 49/00
[52] U.S. Cl. ............................................. 424/1.69
[58] Field of Search .................. 424/1.1, 1.45, 1.69, 424/1.49; 530/300, 311, 345

[56] References Cited

U.S. PATENT DOCUMENTS

| | | | |
|---|---|---|---|
| 4,434,151 | 2/1984 | Byrne et al. | 424/1.1 |
| 4,444,690 | 4/1984 | Fritzberg | 260/429 |
| 4,472,509 | 9/1984 | Gansow et al. | 436/548 |
| 4,485,101 | 11/1984 | Coy et al. | 424/177 |
| 4,571,430 | 2/1986 | Byrne et al. | 560/148 |
| 4,575,556 | 3/1986 | Byrne et al. | 549/63 |
| 4,853,371 | 8/1989 | Coy et al. | 514/12 |
| 4,861,869 | 8/1989 | Nicolotti et al. | 530/402 |
| 4,871,717 | 10/1989 | Coy et al. | 514/11 |
| 4,877,868 | 10/1989 | Reno et al. | 424/1.1 X |
| 4,904,642 | 2/1990 | Coy et al. | 514/11 |
| 5,078,985 | 1/1992 | Rhodes | 424/1.1 |
| 5,096,696 | 3/1992 | Galanakis | 424/1.1 |
| 5,116,596 | 5/1992 | Bremer et al. | 424/1.1 |
| 5,128,119 | 7/1992 | Griffiths | 424/1.1 |
| 5,177,192 | 1/1993 | Pak et al. | 424/1.1 X |
| 5,196,510 | 3/1993 | Rodwell et al. | 424/1.1 X |
| 5,225,180 | 7/1993 | Dean et al. | 424/1.1 |

FOREIGN PATENT DOCUMENTS

| | | | |
|---|---|---|---|
| 135160 | 3/1985 | European Pat. Off. | A61K 49/02 |
| 188256 | 7/1986 | European Pat. Off. | A61K 49/02 |
| 237150 | 9/1987 | European Pat. Off. | A61K 49/02 |
| 284071 | 9/1988 | European Pat. Off. | A61K 49/02 |
| 389180 | 9/1990 | European Pat. Off. | C07K 7/06 |
| 2225579 | 6/1990 | United Kingdom | A61K 49/02 |
| 88/07382 | 10/1988 | WIPO | A61K 49/02 |
| 89/04666 | 6/1989 | WIPO | A61K 37/24 |
| 91/01144 | 2/1991 | WIPO | A61K 49/02 |
| 92/21383 | 12/1992 | WIPO | A61K 49/02 |

OTHER PUBLICATIONS

Cox, P. H. et al., European Journal of Nuclear Medicine, vol. 18, No. 8, p. 558, Aug. 1991.
Sundrehagen, Int. J. Appl. Radiat. Isot., vol 34, No. 7, pp. 1003-1007, 1983.
Rhodes, Sem. Necl. Med. 4: 281-293 (1974).
Davison et al., Inorg. Chem. 20: 1629-1632 (1981).
Fritzberg et al., J. Nucl. Med. 23: 592-598 (1982).
Khaw et al., J. Nucl. Med. 23: 1011-1019 (1982).
Bryne and Tolman, J. Nucl. Med. 24: P126 (1983).
Bryson et al., Inorg. Chem. 27: 2154-2161 (1988).
Bakker et al., J. Nucl. Med. 31: 1501-1509 (1990).
Bryson et al., Inorg. Chem. 29: 2948-2951 (1990).
Kwekkeboom et al., J. Nucl. Med. 32: 981 (1991).
Bakker et al., J. Nucl. Med. 32: 1184-1189 (1991).
Larson, J. Nucl. Med. 32: 1189-1191 (1991).
Albert et al., Abstract LM10, 12th American Peptide Symposium: 1991.
Cox et al., Abstract, 7th International Symposium on Radiopharmacology, (1991).
Fischman et al., "A Ticket to Ride: Peptide Radiopharmaceuticals," *J. Nuc. Med.* 34 (12), Dec. 1993, pp. 2253-2263.

*Primary Examiner*—Robert L. Stoll
*Assistant Examiner*—Lara E. Chapman
*Attorney, Agent, or Firm*—Allegretti & Witcoff, Ltd.

[57] ABSTRACT

The invention relates to radiolabeled imaging of a mammalian body. The invention in particular provides for reagents labeled with technetium-99m for such imaging. The invention specifically provides somatostatin, somatostatin derivatives, somatostatin analogues or peptides that bind to the somatostatin receptor and contain at least 2 cysteine residues that form a disulfide or wherein the disulfide is reduced to the sulfhydryl form that are labeled with technetium-99m and that can be targeted to specific sites within a mammalian body for imaging.

10 Claims, No Drawings

TECHNETIUM-99M LABELED SOMATOSTATIN-DERIVED PEPTIDES FOR IMAGING

This is divisional application of U.S. patent application Ser. No. 07/757,470, filed Sep. 10, 1991, now U.S. Pat. No. 5,225,180, issued Jul. 6, 1993.

BACKGROUND OF THE INVENTION

1. Field of the Invention

This invention relates to radiodiagnostic reagents and peptides, and methods for producing labeled radiodiagnostic agents. Specifically, the invention relates to technetium99m (Tc-99m) labeled reagents, methods and kits for making such reagents, and methods for using such reagents. In particular, the invention relates to Tc-99m labeled somatostatin, derivatives of somatostatin, analogues of somatostatin or peptides that bind to the somatostatin receptor and contain at least 2 cysteine residues that form a disulfide or wherein the disulfide is reduced to the sulfhydryl form.

2. Description of the Prior Art

Somatostatin is a tetradecapeptide that is endogenously produced by the hypothalamus and pancreas in humans and other mammals. The peptide has the formula:

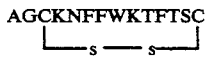  Formula I

[Single letter abbreviations for amino acids can be found in G. Zubay, Biochemistry (2d ed.), 1988, (MacMillan Publishing: New York), p.33]. This peptide exerts a wide variety of biological effects in vivo. It is known to act physiologically on the central nervous system, the hypothalamus, the pancreas, and the gastrointestinal tract. Somatostatin exerts it effects by binding to specific receptors expressed at the cell surface of cells comprising these organs. In addition, these high-affinity binding sites have been found to be abundantly expressed at the cell surface of most endocrine-active tumors arising from these tissues. Thus, the expression of high-affinity binding sites for somatostatin is a marker for these tumor cells, and specific binding with somatostatin can be exploited to locate and identify tumor cells in vivo.

One method that can readily be adapted to enable detection of tumor cells in vivo based on their expression of high affinity binding sites for somatostatin is radioimaging. Radionuclides which emit high energy gamma radiation can be readily detected by scintigraphy after injection into a human or an animal. A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. The sensitivity of imaging methods using radioactively-labeled peptides is much higher than other techniques known in the art, since the specific binding of the radioactive peptide concentrates the radioactive signal over the cells of interest, for example, tumor cells. This is particularly important for endocrine-active gastrointestinal tumors, which are usually small, slow-growing and difficult to detect by conventional methods.

Preparation of somatostatin analogues and uses for such analogues is known in the prior art.

Coy et al., U.S. Pat. No. 4,853,371 disclose synthetic octapeptide somatostatin analogues.

Coy and Murphy, U.S. Pat. No. 4,871,717 disclose synthetic heptapeptide somatostatin analogues.

Coy and Murphy, U.S. Pat. No. 4,485,101 disclose synthetic dodecapeptide somatostatin analogues.

Coy et al., U.S. Pat. No. 4,904,642 disclose synthetic octapeptide somatostatin analogues.

Taylor et al., European Patent Application No. WO 89/04666 disclose a method of treating cancer in an animal by administering at least a minimal dose of a hexapeptide analog of somatostatin.

Eck and Moreau, European Patent Application No. 90302760.5 disclose therapeutic octapeptide somatostatin analogues.

Methods for radiolabeling somatostatin analogues that have been modified so as to contain a tyrosine amino acid (Tyr or Y) are known in the prior art.

Albert et al., UK Patent Application 8927255.3 disclose radioimaging using somatostatin derivatives such as octreotide labeled with $^{123}$I.

Bakker et al., J. Nucl. Med. 31: 1501–1509 (1990) describe radioactive iodination of a somatostatin analog and its usefulness in detecting tumors in vivo.

Bakker et al., J. Nucl. Med. 32:1184–1189 (1991) teach the usefulness of radiolabeled somatostatin for radioimaging in vivo.

The use of chelating agents for radiolabeling polypeptides is known in the prior art.

Byrne et al., U.S. Pat. No. 4,434,151 describe novel homocysteine thiolactone bifunctional chelating agents for chelating radionuclides which can couple radionuclides to terminal amino-containing compounds capable of localizing in an organ or tissue which is desired to be imaged.

Fritzberg, U.S. Pat. No. 4,444,690 describes a series of technetium-chelating agents based on 2,3-bis(mercaptoacetamido) propanoate.

Gansow et al., U.S. Pat. No. 4,472,509 teach methods of manufacturing and purifying metal chelate-conjugated monoclonal antibodies.

Byrne et al., U.S. Pat. Nos. 4,571,430 and 4,575,556 describe novel homocysteine thiolactone bifunctional chelating agents for chelating radionuclides that can couple radionuclides to terminal amino-containing compounds capable of localizing in an organ or tissue which is desired to be imaged.

Nicolotti et al., U.S. Pat. No. 4,861,869 describe bifunctional coupling agents useful in forming conjugates with biologically molecules such as antibodies. This reference describes compounds such as S-benzoylmercaptoacetylglycyl-glycylglycine.

European Patent Application 84109831.2 describes technetium chelating complexes of bisamido-bisthio-ligands and salts thereof, used primarily as renal function monitoring agents.

European Patent Application No. 86100360.6 describes dithio, diamino, or diamidocarboxylic acids or amine complexes useful for making technetium imaging agents.

European Patent Application 88104755.9 describes various S-protected mercaptoacetylglycylglycine chelating groups bound to large proteins such as antibodies.

Davison et at., Inorg. Chem. 20: 1629–1632 ( 1981 ) disclose a novel class of oxotechnetium chelate complexes.

Fritzberg et al., J. Nucl. Med. 23:592–598 (1982) disclose a technetium chelating agent based on N,N'-bis(-mercaptoacetyl)-2,3-diaminopropanoate.

Byrne and Tolman, J. Nucl. Med. 24:P126 (1983) disclose a bifunctional thiolactone chelating agent for coupling Tc-99m to biological molecules.

Bryson et al., Inorg. Chem. 27:2154–2161 (1988) describe thiolate ligands for complexing with technetium.

Bryson et al., Inorg. Chem. 29:2948–2951 (1990) describe thiolate ligands for complexing with technetium.

Methods for radiolabeling somatostatin by covalently modifying the peptide to contain a metal chelating group has been disclosed in the prior art.

Albert et al., UK Patent Application 8927255.3 disclose radioimaging using somatostatin derivatives such as octreotide labeled with $^{111}$In via a chelating group bound to the amino-terminus.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Kwekkeboom et al., J. Nucl. Med. 32:981 (1991) Abstract #305 relates to radiolabeling somatostatin analogues with $^{111}$In.

Albert et al., Abstract LM10, 12th American Peptide Symposium: 1991 describe uses for $^{111}$In-labeled diethylene-triaminopentaacetic acid-derivatized somatostatin analogues.

Methods for labeling peptides and polypeptides with Tc-99m have been disclosed in the prior art.

Dean, co-pending U.S. patent application Ser. No. 07/653,012 teaches reagents and methods for preparing peptides comprising a Tc-99m chelating group covalently linked to a specific binding peptide for radioimaging in vivo, and is hereby incorporated by reference.

Fritzberg, U.S. Pat. No. 4,444,690 describes a series of technetium-chelating agents based on 2,3-bis(mercaptoacetamido) propanoate.

Gansow et al., U.S. Pat. No. 4,472,509 teach methods of manufacturing and purifying Tc-99m chelate-conjugated monoclonal antibodies.

Reno and Bottino, European Patent Application 87300426.1 disclose radiolabeling antibodies with Tc-99m.

Pak et al., European Patent Application No. WO 88/07382 disclose a method for labeling antibodies with Tc-99m.

Rhodes, Sem. Nucl. Med. 4:281–293 (1974) teach the labeling of human serum albumin with technetium-99m.

Khaw et al., J. Nucl. Med. 23:1011–1019 (1982) disclose methods for labeling biologically active macromolecules with Tc-99m.

Byrne and Tolman, supra, disclose a bifunctional thiolactone chelating agent for coupling Tc-99m to biological molecules.

Cox et al., Abstract, 7th International Symposium on Radiopharmacology, p. 16, 1991, disclose the use of $^{131}$I- and $^{111}$In-labeled somatostatin analogues in radiolocalization of endocrine tumors in vivo by scintigraphy. Somatostatin labeled with technetium-99m under reducing conditions was used to scintigraphically localize colorectal carcinoma in rats following intravenous administration. Tc-99m labeled somatostatin was prepared by incubating the peptide with a solid phase electron donor and sodium pertechnetate at room temperature. Labeling efficiencies of 100% were obtained, with excess free technetium found to bind to the electron donor leaving only labeled complex in solution. Following intravenous administration in rats, rapid blood clearance was observed with accumulation in liver, kidneys and bladder; tumor uptake was found to achieve maximum levels at approximately 4 rain post-injection. Tumor-to-muscle uptake ratios were 5:1 which compared favorably with ratios of 3:1 reported for the $^{131}$I- and $^{111}$In-labeled analogues. The relationship of tumor label uptake to somatostatin binding was confirmed by a demonstration that somatostatin receptors blocked with suramin showed suppressed tumor uptake of the label.

The present invention provides peptides which are comprised of between 5 and 100 amino acid residues and at least 2 cysteine residues capable of forming a disulfide bond and that are labeled with Tc-99m. The preferred embodiments of the present invention are peptides that are somatostatin, derivatives of somatostatin, analogues of somatostatin or peptides that bind to the somatostatin receptor and contain at least 2 cysteine residues that form a disulfide or wherein the disulfide is reduced to the sulfhydryl form, and that are labeled with Tc-99m. Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides have effective half-lives which are much longer (for example, $^{111}$In, which has a half-life of 60–70 h) or are toxic (for example, $^{125}$I). Although Tc-99m is an ideal radiolabeling reagent, it has not been widely used in the an prior to the present invention [see, for example, Lamberts, J. Nucl. Meal. 32:1189–1191 (1991)].

Another advantage of the present invention is that the radioactively-labeled somatostatin, somatostatin derivatives, somatostatin analogues or peptides that bind to the somatostatin receptor and contain at least 2 cysteine residues that form a disulfide or wherein the disulfide is reduced to the sulfhydryl form provided by the invention have Tc-99m covalently linked to both of the cysteine-derived sulfur atoms capable of forming a disulfide bond of the peptide. Thus, the label can be directly linked to the peptide. The advantage over the prior art is that the invention avoids the necessity of providing somatostatin analogues which contain at least one tyrosine residue to enable radioactive iodine labeling. The invention also does not require the covalent linkage of heterologous chelating groups, described in the prior art. In addition, peptides according to the present invention can be prepared according to the methods of the invention from any available source of somatostatin, somatostatin derivative, somatostatin analog or peptide that binds to the somatostatin receptor and contains at least 2 cysteine residues that form a disulfide or wherein the disulfide is reduced to the sulfhydryl form, without the need to synthesize a derivative of a particular design or having specific metal ion chelating properties in addition to its biological specificity. The use of native somatostatin enabled by the invention also provides labeled peptides of well characterized binding specificity in vivo.

Thus the present invention provides Tc-99m radiolabeled peptides and radioimaging agents related to somatostatin and its derivatives or analogues, or indeed any peptide that binds to the somatostatin receptor and contains at least 2 cysteine residues that form a disulfide or wherein the disulfide is reduced to the sulfhydryl form, for use in imaging tumors and other tissues in vivo. The advantages of the invention include the use of Tc-99m as radionuclide, radiolabeling of native as well as modified somatostatin directly via the sulfhydryl groups of at least 2 cysteine residues of the peptide and the ability to utilize any available source of somatostatin, somatostatin derivative, somatostatin analog or peptide that binds to the somatostatin receptor and contains at least 2 cysteine residues that form a disulfide or wherein the disulfide is reduced to the sulfhydryl form, without requiring any particular modifications of the peptide.

SUMMARY OF THE INVENTION

The invention encompasses somatostatin and peptide derivatives of somatostatin labeled with technetium-99m (Tc-99m) useful for imaging target sites within a mammalian body. The invention also encompasses methods for making (Tc-99m)-labeled somatostatin, derivatives of somatostatin, analogues of somatostatin or peptides that bind to the somatostatin receptor and contain at least 2 cysteine residues that form a disulfide or wherein the disulfide is reduced to the sulfhydryl form, and methods for using (Tc-99m)-labeled somatostatin and peptide derivatives of somatostatin to image target sites within a mammalian body. The invention also includes complexes of Tc-99m with somatostatin, somatostatin derivatives, somatostatin analogues or peptides that bind to the somatostatin receptor and contain at least 2 cysteine residues that form a disulfide or wherein the disulfide is reduced to the sulfhydryl form, methods for making such complexes and methods for using these complexes to image target sites within a mammalian body.

DETAILED DESCRIPTION OF THE INVENTION

The present invention provides technetium-99m labeled peptides for imaging target sites within a mammalian body that comprise between 5 and 100 amino acid residues and at least 2 cysteine residues capable of forming a disulfide bond, reacted with technetium-99m under reducing conditions. For purposes of this invention, the phrase "under reducing conditions" is intended to describe reaction of the peptides of the invention with technetium99m in the presence of a reducing agent; in preferred embodiments, the reducing agent is either stannous chloride or a solid-phase reducing agent. Alternatively, the peptides of the invention are reacted with the reducing agent prior to reaction with technetium-99m, so that the peptides are reacted with technetium-99m in a reduced form. In another alternative, both the peptides of the invention and technetium-99m are reacted with a reducing agent prior to being reacted with each other; preferred reducing agents are stannous chloride and a solid-phase reducing agent. The methods of the invention are also intended to encompass reaction of pre-reduced or unreduced technetium-99m in the presence of a reducing agent with peptides containing native sulfhydryl groups in the reduced form. All of these reaction conditions are intended to be described by the phrase "under reducing conditions".

The invention particularly provides radioactively-labeled somatostatin, somatostatin derivatives, somatostatin analogues or peptides that bind to the somatostatin receptor. Somatostatin provided by the invention includes commercially available preparations of somatostatin as well as somatostatin prepared as described in Example 1 hereinafter. Somatostatin derivatives, analogues and peptides that bind to the somatostatin receptor include but are not limited to any peptide sequence comprised of between 5 and 100 amino acid residues and at least 2 cysteine residues separated by at least one other amino acid and capable of forming a disulfide bond, and exhibiting the biological binding properties of native somatostatin or any modification of those properties, wherein the peptide retains specific binding characteristics that are identical to, similar with or distinct from the native somatostatin peptide. Derivatives are intended to mean modifications in the composition, identity and derivitization of the amino acid components of the peptide, provided that the peptide sequence is comprised of at least 2 cysteine residues separated by at least one other amino acid and capable of forming a disulfide bond, and the peptide retains the specific biological binding properties to the somatostatin receptor of native somatostatin. These modifications include compositions comprised of the D- as well as the native L-stereoisomers of any of the component amino acids of the peptide; substitution in the aromatic sidechain of any component amino acid (for example, F, Y or W); derivitization of the amino- or carboxyl-groups in the sidechains of any component amino acid (for example, D, E, K, N or Q), or substitutions in the amino-or carboxyl-terminus of the peptide, or wherein the peptide is covalently linked at either the amino- or carboxyl-terminus to any other protein, peptide or biologically active molecule, or cyclization of the peptide. [Single letter abbreviations for amino acids can be found in G. Zubay, supra]. Somatostatin derivatives are intended to include peptides comprised of amino acids which are naturally occurring or not naturally-occurring amino acids. Although the present invention is specifically intended to relate to radiolabeling of somatostatin, somatostatin derivatives, somatostatin analogues or peptides that bind to the somatostatin receptor and contain at least 2 cysteine residues capable of forming a disulfide bond, the methods of the invention are applicable to any peptide or polypeptide provided the peptide or polypeptide is comprised of at least 2 cysteine residues separated by at least one other amino acid and capable of forming a disulfide bond, and the scope of the invention is intended to encompass such other peptides and polypeptides.

The invention provides Tc-99m labeled somatostatin, somatostatin derivatives, somatostatin analogues or peptides that bind to the somatostatin receptor that are labeled as a result of the formation of coordinate covalent linkage of the Tc-99m atom to 2 of the cysteine-derived sulfur atoms comprising the cysteine residues of the peptide. This method of directly labeling somatostatin or somatostatin derivatives, analogues or related peptides is advantageous over the methods known in the prior art. Methods of radioactively labeling somatostatin or related peptides known prior to the present invention required the use of substituted somatostatin derivatives that were comprised of at least one tyrosine residue in order to permit radioiodination of the peptide. Alternatively, radiolabeled somatostatin peptides have been made by covalent linkage of a metal chelating group to the amino terminus of the peptide and reaction with the radionuclide. A particular disadvantage of the covalent attachment of these chelating groups is that the presence of these groups at the amino terminus of the peptide might interfere with the biological properties of the peptides in vivo and in addition may intrinsically cause biocompatability problems either itself or when linked to another peptide. Labeled peptides of the present invention can be prepared directly from commercially available somatostatin or any somatostatin derivative, analog or related peptide of sufficient purity or synthesized by means well known to those with skill in the art. An additional advantage of the peptides of this invention and those prepared by the methods of the invention is that these peptides contain Tc-99m covalently linked to the peptides, thus providing a reagent with maximum stability due to the nature of the Tc-peptide bond.

In forming a complex of radioactive technetium with the peptides of this invention, the technetium complex, preferably a salt of Tc-99m pertechnetate, is reacted with the peptides of this invention in the presence of a reducing agent; in a preferred embodiment, the reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of the somatostatin, somatostatin derivatives, somatostatin analogues or peptides that bind to the somatostatin receptor and contain at least 2 cysteine residues that form a disulfide or wherein the disulfide is reduced to the sulfhydryl form that are to be labeled and a sufficient amount of reducing agent to label the peptide with Tc-99m. Alternatively, the complex may be formed by reacting the peptides of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. The reaction of the peptides of this invention with Tc-pertechnetate or preformed Tc-99m labile complex can be carried out in an aqueous medium at room temperature. The artionic complex which has a charge of $[-1]$ is formed in the aqueous medium in the form of a salt with a suitable cation such as sodium cation, ammonium cation, mono, di- or tri-lower alkyl amine cation, etc. Any conventional salt of the artionic complex with a pharmaceutically acceptable cation can be used in accordance with this invention.

In another embodiment of the present invention, the somatostatin, somatostatin derivatives, somatostatin analogues or peptides that bind to the somatostatin receptor and contain at least 2 cysteine residues capable of forming a disulfide bond that are to be labeled are reduced prior to labeling by incubating the peptides with a reducing agent. In a preferred embodiment, the reducing agent is stannous chloride. In an additional preferred embodiment, the reducing agent is a solid-phase reducing agent. The pre-reduced peptide is then labeled by reaction with a Tc-99m under reducing conditions or with pre-reduced Tc99m or Tc-99m complex.

In a preferred embodiment of the invention, a kit for preparing technetium-labeled peptides is provided. Peptides that are somatostatin, somatostatin derivatives, somatostatin analogues or peptides that bind to the somatostatin receptor and contain at least 2 cysteine residues capable of forming a disulfide bond are chemically synthesized using methods and means well-known to those with skill in the art and described hereinbelow in Example 1. Peptides thus prepared are comprised of at least 2 cysteine residues, wherein the sulfhudryl groups of the cysteine residues are in the reduced form. An appropriate amount of the peptide is introduced into a vial containing a reducing agent, such as stannous chloride or a solid-phase reducing agent, in an amount sufficient to label the peptide with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 2 hereinbelow.

Radioactively labeled peptides provided by the present invention are provided having a suitable amount of radioactivity. In forming the Tc-99m radioactive anionic complexes, it is generally preferred to form radioactive complexes in solutions containing radioactivity at concentrations of from about 0.01 millicurie (mCi) to 100 mCi per ml.

Technetium labeled somatostatin, somatostatin derivatives, somatostatin analogues or peptides that bind to the somatostatin receptor can be used for visualizing organs such as the kidney for diagnosing disorders in these organs, and tumors, in particular gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. In accordance with this invention, the technetium labeled peptides or anionic complexes either as a complex or as a salt with a pharmaceutically acceptable cation are administered in a single unit injectable dose. Any of the common carriers such as sterile saline solution, plasma, etc., can be utilized after the radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of imaging for diagnostic purposes can be utilized in accordance with this invention.

The technetium labeled peptides and complexes may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these peptides are more fully illustrated in the following examples.

These examples are provided for illustrating the invention and are not meant to be construed as limiting.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with either dicyclohexylcarbodiimide/hydroxybenztriazole (DCC/HOBT) or 2-(1H-benzo-triazol-1-yl)-1,1,3,3-tetramethyluronium hexafluorophosphate/hydroxybenztriazole (HBTU/HOBT), and p-hydroxymethylphenoxy-methylpolystyrene (HMP) resin for carboxyl-terminus acids or Rink amide resins for carboxyl-terminus amides. Resin-bound products were routinely cleaved using a solution of comprised of trifluoroacetic acid, water, phenol, thioanisole, and ethanedithiol, prepared in ratios of 90:5:7.5:5:2.5 for 1.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

Acyclopeptides thus prepared may be then cyclized by the formation of an intramolecular disulfide bond either before or after HPLC purification in solution at pH 8.0 either chemically using $K_3Fe(CN)_6$ or spontaneously catalyzed by air. Cyclized peptides are purified by HPLC as described above.

EXAMPLE 2

Somatostatin Labeling with Technetium-99m

Somatostatin was labeled with technetium-99m (Tc-99m) using the following protocols.

Direct Reduction Method. 0.66 µmoles somatostatin-14 (S-14=Formula I; Bachem Bioscience Inc., Cat# H-1490) were reduced using an immobilized reductant (Reduce-Imm ™ Reducing Kit, Pierce Chemical Co., Cat# 77700H), a reagent for column-based reduction of disulfides consisting of a proprietary solid phase reductant cross-linked to 6% beaded agarose. Disulfide reduction using this reagent results in a 98.6% yield of expected reduced thiol (SH) as determined by Ellman's assay [Ellman, Arch. Biochem. Biophys. 74:443 (1958)]. (Tc-99m)-labeling was accomplished by incubating 100nM SH equivalents of S-14 (117µl) with 0.6mCi (29µl) Tc-99m gluceptate at room temperature for 15 min. Tc-99m gluceptate was prepared by reconstituting a Glucoscan Vial (E.I. DuPont DeNemours, Inc., Wilmington, Del.) with 1.0 ml Tc-99m sodium pertechnetate containing 21mCi.

The extent of Tc-99m peptide labeling achieved was determined by thin layer chromatography (TLC) using Merck silica gel 60 $F_{250}$ aluminum-backed strips spotted with 10 µl of sample and chromatographed with acetone or phosphate buffered saline (PBS). Under these conditions, 99% of (Tc-99m)-associated radioactivity remained at the origin ($R_f$=0.0) in either solvent, indicating that no significant concentration of free Tc-99m pertechnetate or Tc-99m gluceptate could be detected in the sample. Purity of the 99m-Tc-labeled peptide was determined by HPLC using a Vydak 218TP54 analytical column (RP-18, 5 micron, 250ram long) eluted with a gradient that ranged from 0% Solution A ($CH_3CN:H_2O:TFA$, 90:10:0.1) and 100% Solution B (0.1% TFA in water) to 100% Solution A and 0% Solution B achieved over 10 rain, with conditions of 100% Solution A and 0% Solution B maintained for the remainder of the chromatographic run. An in-line NaI detector was used to determine that 98.9% of the radiometric species existed as a single peak with a retention time of 14.5 min. In contrast, unconjugated Tc-99m pertechnetate and Tc-99m gluceptate eluted from this column within 1–4 min under these conditions, confirming the successful labeling of somatostatin with Tc-99m using this method.

Stannous Chloride Method. A stannous chloride solution was fleshly prepared by dissolving 26.5 mg $SnCl_2$ in 1.128 ml 1N HCl. A gluconate solution was prepared by dissolving 500 mg of the potassium salt of D-gluconic acid in 50 mM phosphate buffer and adjusting the pH to 7.4 with 1N NaOH or 1N HCl. The gluconate solution was deoxygenated by bubbling treatment with nitrogen gas. 17 µl (equivalent to 400 µg) of the stannous chloride solution plus 17 µl N NaOH were added to 1.0 ml of the gluconate solution to prepare the peptide reconstitution solution.

55.5 nmoles of S-14 (0.09 mg) were dissolved in 1.0 ml of the peptide reconstitution solution prepared as described above and then incubated for 3 h at room temperature prior to the addition of 250 µl Tc-99m (6.5mCi) sodium pertechnetate (sample #1).

Alternatively, 86.3 nmoles of S-14 (0.14rag) were dissolved in 1.0 ml of the peptide reconstitution solution 5 minutes prior to the addition of 250 µl Tc-99m (6.5mCi) sodium pertechnetate (sample #2).

Somatostatin in both samples was labeled with Tc-99m by incubating the samples at room temperature for 60 min. The extent of Tc-99m peptide labeling was determined by TLC using Merck silica gel 60 F250 aluminum-backed strips spotted with 10 µl of sample and chromatographed in acetone or PBS. After 60 min, both samples exhibited at least 94% of the radioactivity at the origin ($R_f$=0.0) in both solvents, demonstrating that no significant concentration of free Tc-99m pertechnetate or Tc-99m gluconate could be detected in either sample.

Tc-99m purity was determined by HPLC using a Vydak 218TP54 analytical column and eluted as described above. An in-line NaI detector was used to evaluate the distribution or radiometric species in each sample. Sample #1 exhibited 91% of detected radioactivity as a single species with a retention time equivalent to 14.5 min. Sample #2 exhibited 96% of detected radioactivity as 4 separate species with retention times of 19.4 rain (68% of total detected radioactivity), 20.2 rain (17%), 20.9 rain (7%), and 21.5 rain (4%). Unconjugated Tc-99m pertechnetate and Tc-99m gluconate elute within 1–4 minutes under these conditions. These results confirm the successful labeling of somatostatin with Tc-99m using either variation of this method.

What is claimed is:

1. A method for preparing a technetium-99m labeled peptide for imaging target sites within a mammalian body by directly labeling a homogeneous preparation of a peptide, wherein the peptide comprises between 5 and 40 amino acid residues and contains 2 cysteine residues capable of forming a disulfide bond, the method comprising reacting the peptide with technetium-99m under reducing conditions.

2. A method for preparing a technetium-99m labeled peptide for imaging target sites within a mammalian body by directly labeling a homogeneous preparation of a peptide that binds to the somatostatin receptor and comprises between 5 and 40 amino acid residues and contains 2 cysteine residues capable of forming a disulfide bond, the method comprising reacting the peptide with technetium-99m under reducing conditions.

3. The method of claim 1, wherein said reducing conditions comprise reacting the reagent in the presence of a stannous ion or a solid phase reducing agent.

4. A method for directly labeling a reagent for preparing a technetium-99m labeled peptide for imaging target sites within a mammalian body, the reagent comprising a homogeneous preparation of a peptide wherein the peptide comprises between 5 and 40 amino acid residues and at least 2 cysteine residues capable of forming a disulfide bond, the method comprising:

(a) reacting the peptide under reducing conditions to produce a reduced-thiol peptide; and b) reacting the reduced-thiol peptide with a prereduced technetium-99m complex.

5. A method for preparing a technetium-99m labeled peptide for imaging target sites within a mammalian body by directly labeling a homogeneous preparation of a peptide that binds to the somatostatin receptor and comprises between 5 and 40 amino acid residues and contains 2 cysteine residues capable of forming a disulfide bond, the method comprising:.

(a) reacting the peptide under reducing conditions to produce a reduced-thiol peptide; and (b) reacting the reduced-thiol peptide with a prereduced technetium-99m complex.

6. A kit for preparing a radiopharmaceutical preparation, said kit comprising a sealed vial containing a predetermined quantity of a reagent for preparing a technetium-99m labeled peptide for imaging target sites within a mammalian body, the reagent comprising a homogeneous preparation of a peptide wherein the peptide comprises between 5 and 40 amino acid residues and at least 2 cysteine residues capable of forming a disulfide bond, wherein the reagent is directly labeled with technetium-99m by reaction with technetium99m under reducing conditions, and a sufficient amount of a reducing agent to label said compound with technetium-99m.

7. A kit for preparing a radiopharmaceutical preparation for imaging target sites within a mammalian body, the radiopharmaceutical preparation comprising a technetium-99m labeled peptide, said kit comprising a sealed vial containing a predetermined quantity of a homogeneous preparation of a peptide that binds to the somatostatin receptor and comprises between 5 and 40 amino acid residues and contains 2 cysteine residues that form a disulfide or wherein the disulfide is reduced to the sulfhydryl form, the kit further comprising a sufficient amount of a reducing agent to label said peptide with technetium-99m, wherein the peptide is directly labeled with technetium-99m by reaction with technetium-99m under reducing conditions.

8. The method of claim 2, wherein the peptide is somatostatin or a derivative or analog thereof.

9. The method of claim 5, wherein the peptide is somatostatin or a derivative or analog thereof.

10. The kit according to claim 7 wherein the peptide is somatostatin or a derivative or analog thereof.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 2..14
    (D) OTHER INFORMATION: /label=Disulfide-bond
      / note="The sidechain thiol groups of the third
      residue cysteine and the carboxy-terminal cysteine
      form a disulfide bond in native somatostatin (xi) SEQUENCE DESCRIPTION: SEQ ID NO:1:

Ala  Gly  Cys  Lys  Asn  Phe  Phe  Trp  Lys  Thr  Phe  Thr  Ser  Cys
  1              5                        10